(12) United States Patent  
Koenemann et al.

(10) Patent No.: US 7,741,487 B2
(45) Date of Patent: Jun. 22, 2010

(54) METHOD FOR PRODUCING QUATERRYLENE-3,4:13,14-TETRACARBOXY DIIMIDES BY DIRECT SYNTHESIS

(75) Inventors: Martin Koenemann, Mannheim (DE); Arno Boehm, Langenfeld (DE); Hermann Bidlingmaier, Sachsenheim (DE); Reinhold Rieger, Waldsee (DE); Peter Blaschka, Ludwigshafen (DE); Helmut Reichelt, Neustadt (DE); Matthias Krieger, Basel (CH)

(73) Assignee: BASF Aktiengesellschaft, Ludwigshafen (DE)

( * ) Notice: Subject to any disclaimer, the term of this patent is extended or adjusted under 35 U.S.C. 154(b) by 791 days.

(21) Appl. No.: 11/573,948

(22) PCT Filed: Aug. 4, 2005

(86) PCT No.: PCT/EP2005/008443

§ 371 (c)(1),
(2), (4) Date: Feb. 20, 2007

(87) PCT Pub. No.: WO2006/021307

PCT Pub. Date: Mar. 2, 2006

(65) Prior Publication Data

US 2009/0030206 A1   Jan. 29, 2009

(30) Foreign Application Priority Data

Aug. 26, 2004 (DE) ........................ 10 2004 041 604

(51) Int. Cl.
C07D 471/02 (2006.01)
C07D 221/18 (2006.01)
(52) U.S. Cl. .......................................... 546/26; 546/38
(58) Field of Classification Search ................ 546/26, 546/38
See application file for complete search history.

(56) References Cited

FOREIGN PATENT DOCUMENTS

| DE | 195 12 773 | 10/1996 |
| DE | 102 33 955 | 6/2004 |
| EP | 0 596 292 | 5/1994 |

OTHER PUBLICATIONS

Heinz Langhals, et al., "A Two-Step Synthesis of Quaterrylenetetracarboxylic Bisimides—Novel NIR Fluorescent Dyes", Tetrahedron Letters, vol. 36, No. 36, XP 004027248, pp. 6423-6424, 1995.
Heribert Quante, et al., "Quaterrylentetracarbonsaurediimide", Angewandte Chem., vol. 107, No. 12, pp. 1487-1489, 1995.
Suk-Wah Tam-Chang, et al., "Synthesis and Studies of the Properties of a Liquid-Crystalline Quaterrylenebis (Dicarboximide) by 1H NMR and UV-VIS Spectroscopies", J.Org. Chem., vol. 69, pp 2719-2726, 2004.

*Primary Examiner*—Charanjit S Aulakh
(74) *Attorney, Agent, or Firm*—Oblon, Spivak, McClelland, Maier & Neustadt, L.L.P.

(57) ABSTRACT

A process for preparing quaterrylene-3,4:13,14-tetracarboximides of the general formula I

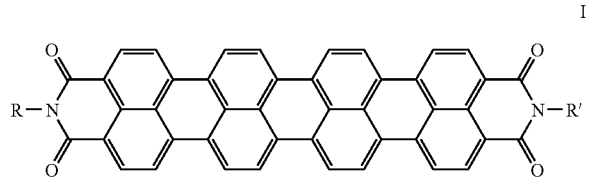

in which
R, R' are each independently hydrogen or optionally substituted $C_1$-$C_{30}$-alkyl, $C_5$-$C_8$-cycloalkyl or aryl or hetaryl;
which comprises reacting a perylene-3,4-dicarboximide of the general formula IIa

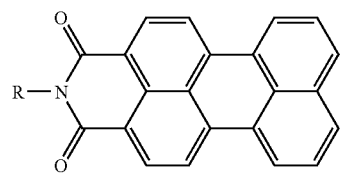

in the presence of a base-stable, high-boiling, organic solvent and of an alkali metal base or alkaline earth metal base, with a perylene-3,4-dicarboximide of the general formula IIb

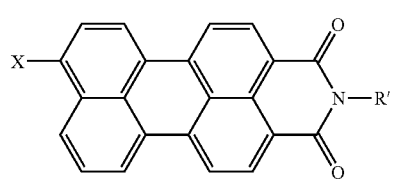

in which X is hydrogen, bromine or chlorine.

7 Claims, No Drawings

METHOD FOR PRODUCING QUATERRYLENE-3,4:13, 14-TETRACARBOXY DIIMIDES BY DIRECT SYNTHESIS

The present invention relates to a novel process for preparing quaterrylene-3,4:13,14-tetracarboximides of the general formula I

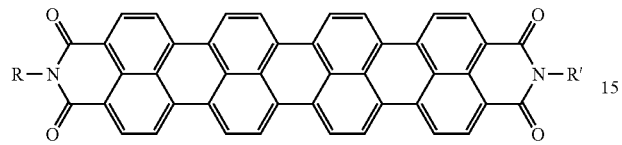

in which the variables are each defined as follows:
R, R' are each independently:
  hydrogen;
  (A) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by:
    (i) $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$; and/or —$POR^2R^3$;
    (ii) aryl or hetaryl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be substituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;
    (iii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;
    (iv) a -U-aryl radical which may be mono- or polysubstituted by the above radicals specified as substituents for the aryl radicals (ii), where U is an —O—, —S—, —$NR^1$—, —CO—, —SO— or —$SO_2$— moiety;
  (B) $C_3$-$C_8$-cycloalkyl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by the (i), (ii), (iii), (iv) radicals, and/or
    (v) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by: $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or saturated or unsaturated $C_4$-$C_7$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties, where the aryl and cycloalkyl radicals may each be mono- or polysubstituted by $C_1$-$C_{18}$-alkyl and/or the above radicals specified as substituents for alkyl;
  (C) aryl or hetaryl, to which may be fused further saturated or unsaturated 5- to 7-membered rings whose carbon skeleton may be interrupted by one or more —O—, —S—, —$NR^1$—, —N=$CR^1$—, —C≡C—, —$CR^1$=$CR^1$—, —CO—, —SO— and/or —$SO_2$— moieties, where the entire ring system may be substituted by the (i), (ii), (iii), (iv), (v) radicals, and/or aryl- and/or hetarylazo, each of which may be substituted by $C_1$-$C_{10}$-alkyl, $C_1$-$C_6$-alkoxy and/or cyano;
$R^1$ is hydrogen or $C_1$-$C_{18}$-alkyl, where the $R^1$ radicals may be the same or different when they occur more than once;
$R^2$, $R^3$ are each independently hydrogen;
  $C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^1$;
  aryl or hetaryl, to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl.

As is well known, quaterrylene-3,4:13,14-tetracarboximides are of particular interest as pigments and near-IR absorbers.

EP-A-596 292 and Angew. Chem. 107, p. 1487-1489 (1995) for the first time describes the synthesis of N,N'-didodecyl- and N,N'-bis(2,6-diisopropylphenyl)-substituted quaterrylene-3,4:13,14-tetracarboximide. In this reaction, the 9-bromoperylene-3,4-dicarboximide substituted correspondingly on the imide nitrogen atom is converted with elimination of bromine in the presence of an inert diluent (dimethylformamide) and of an organotransition metal catalyst (bis(1,5-cyclooctadiene)nickel) to give the biperylene derivative which is finally converted by heating in an alkaline medium in the presence of an oxidizing agent to the quaterrylene derivative. Disadvantages of this process are that it is restricted to the preparation of certain quaterrylene carboximides and the products comprise catalyst traces which are undesired especially for use in plastics.

DE-A 102 33 955 describes the preparation of N,N'-bis(1-hexylheptyl)quaterrylene-3,4:13,14-tetracarboximide by a likewise two-stage process in the presence of undesired heavy metal catalysts, in whose first step N-(1-hexylheptyl)perylene 3,4-anhydride 9,10-imide is converted in the presence of copper powder to the biperylene derivate, which is oxidized in the second step to the quaterrylene derivative.

Tetrahedron Letters, 36, p. 6423-6424 (1995) discloses the preparation of unsubstituted quaterrylene-3,4:13,14-tetracarboximide and N,N'-bis(1-hexylheptyl) quaterrylene-3,4:13,14-tetracarboximide by heating the corresponding perylene-3,4-dicarboximide to 290-300° C. in 85% by weight potassium hydroxide solution. However, such aggressive reaction conditions place extreme requirements on the apparatus used, and the yield is additionally only 4%.

Finally, J. Org. Chem. 69, p. 2719-2726 (2004) describes N,N'-bis(2-diethylaminoethyl) quaterrylene-3,4:13,14-tetracarboximide as a precursor of the corresponding liquid-crystalline diimide present in anionic form as the acetate. It is prepared by homogeneously coupling the N-(2-diethylaminoethyl)-9-bromoperylene-3,4-dicarboximide prepared over several reaction stages, in the presence of nickel chloride, triphenylphosphine and dimethylformamide. In this specific process too, undesired toxic transition metal catalysts are used.

It is therefore an object of the invention to remedy these disadvantages and to provide a process which enables the preparation of quaterrylene-3,4:13,14-tetracarboximides in an advantageous, economically viable manner.

Accordingly, a process has been found for preparing quaterrylene-3,4:13,14-tetracarboximides of the general formula I

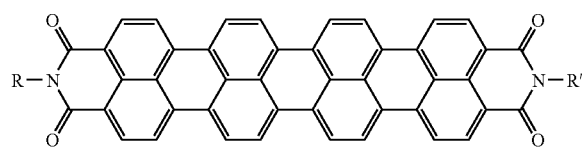

in which the variables are each as defined at the outset, which comprises reacting a perylene-3,4-dicarboximide of the general formula IIa

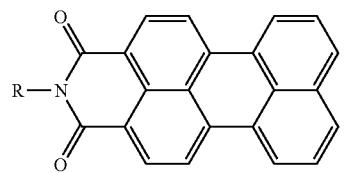

in the presence of a base-stable, high-boiling, organic solvent and of an alkali metal base or alkaline earth metal base, with a perylene-3,4-dicarboximide of the general formula IIb

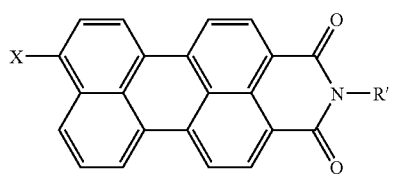

in which X is hydrogen, bromine or chlorine.

Preference is given to using the process according to the invention for preparing quaterrylene-3,4:13,14-tetracarboximides of the formula I, in which the variables are each defined as follows:

R, R' are each independently hydrogen:
  $C_1$-$C_{30}$-alkyl whose carbon chain may be interrupted by one or more —O—, —S—, —$NR^1$—, —CO— and/or —$SO_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical bonded via a nitrogen atom which may contain further heteroatoms and be aromatic;
  $C_5$-$C_8$-cycloalkyl whose carbon skeleton may be interrupted by one or more —O—, —S— and/or —$NR^1$— moieties, and/or which may be mono- or polysubstituted by $C_1$-$C_8$-alkyl;
  aryl or hetaryl which may be mono- or polysubstituted by $C_1$-$C_{18}$-alkyl, $C_1$-$C_6$-alkoxy, cyano, halogen, —$CONHR^2$ and/or aryl- or hetarylazo, each of which may be substituted by $C_1$-$C_{10}$-alkyl, $C_1$-$C_6$-alkoxy or cyano;

$R^1$ is hydrogen or $C_1$-$C_6$-alkyl;
$R^2$ is hydrogen, $C_1$-$C_{18}$-alkyl; aryl or hetaryl, each of which may be substituted by $C_1$-$C_6$-alkyl, $C_1$-$C_8$-alkoxy, halogen, hydroxyl, carboxyl or cyano.

All alkyl groups occurring in the formulae I and II may be straight-chain or branched. When the alkyl groups are substituted, they generally bear 1 or 2 substituents.

Cycloalkyl groups and aromatic radicals which are substituted may generally have up to 3, preferably 1 or 2, of the substituents mentioned.

Specific examples of suitable R, R', $R^1$ and $R^2$ radicals (or their substituents) are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

methoxymethyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trloxadecyl, 3,6,9-trioxaundecyl, 3,6,9-trioxadodecyl, 3,6,9,12-tetraoxatridecyl and 3,6,9,12-tetra-oxatetradecyl;

methylthiomethyl, 2-methylthioethyl, 2-ethylthioethyl, 2-propylthioethyl, 2-isopropylthioethyl, 2-butylthioethyl, 2- and 3-methylthlopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-teiraazatridecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidoburyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthlo, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butyl-phenoxy) carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy) sulfonyl and (4-chlorophenoxy)sulfonyl;

diphenylphosphino, di-(o-tolyl)phosphino and diphenylphosphinoxido;

chlorine, bromine and iodine;

phenylazo, 2-napthylazo, 2-pyridylazo and 2-pyrimldylazo;

phenyl, 1- and 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,3-, 2,4-, 2,5-, 3,5- and 2,6-dimethylphenyl, 2,4,6-trimethylphenyl, 2-, 3- and 4-ethylphenyl, 2,3-, 2,4-, 2,5-, 3,5- and 2,6-diethylphenyl, 2,4,6-triethylphenyl, 2-, 3- and 4-propylphenyl, 2,3-, 2,4-, 2,5-, 3,5- and 2,6-dipropylphenyl, 2,4,6-tripropylphenyl, 2-, 3- and 4-isopropylphenyl, 2,3-, 2,4-, 2,5-, 3,5- and 2,6-diisopropylphenyl, 2,4,6-triisopropylphenyl, 2-, 3- and 4-butylphenyl, 2,3-, 2,4-, 2,5-, 3,5- and 2,6-dibutylphenyl, 2,4,6-tributylphenyl, 2-, 3- and 4-isobutylphenyl, 2,3-, 2,4-, 2,5-, 3,5- and 2,6-diisobutylphenyl, 2,4,6-triisobutylphenyl, 2-, 3- and 4-sec-butylphenyl, 2,3-, 2,4-, 2,5-, 3,5- and 2,6-di-sec-butylphenyl and 2,4,6-tri-sec-butylphenyl, 2-, 3- and 4-tert-butylphenyl, 2,3-, 2,4-, 2,5-, 3,5- and 2,6-di-tert-butylphenyl, 2,4,6-tri-tert-butyl-phenyl; 2-, 3- and 4-methoxyphenyl, 2,3-, 2,4-, 2,5-, 3,5- and 2,6-dimethoxyphenyl, 2,4,6-trimethoxyphenyl, 2-, 3- and 4-ethoxyphenyl, 2,3-, 2,4-, 2,5-, 3,5- and 2,6-di-ethoxyphenyl, 2,4,6-triethoxyphenyl, 2-, 3- and 4-propoxyphenyl, 2,3-, 2,4-, 2,5-, 3,5- and 2,6-dipropoxyphenyl, 2-, 3- and 4-isopropoxyphenyl, 2,3-, 2,4-, 2,5-, 3,5- and 2,6-diisopropoxyphenyl and 2-, 3- and 4-butoxyphenyl; 2-, 3- and 4-chlorophenyl, and 2,3-, 2,4-, 2,5-, 3,5- and 2,6-dichlorophenyl; 2-, 3- and 4-hydroxyphenyl and 2,3-, 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)-aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)-aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl.

With the aid of the process according to the invention, the quaterrylene-3,4;13,14-tetracarboximides I may be prepared in one step by reacting a perylene-3,4-dicarboximide IIa (referred to hereinbelow as imide IIa) with a perylene-3,4-dicarboximide IIb (referred to hereinbelow as imide IIb) in the presence of a base-stable, high-boiling, organic solvent and of an alkali metal base or alkaline earth metal base.

The imide IIb used may be either a 9-halogenated, i.e. chlorinated or in particular brominated, or a nonhalogenated imide which may bear on the imide nitrogen atom an R' radical which may correspond with the R on the imide nitrogen atom of the imide IIa or be different therefrom.

The use of halogenated imide IIb enables the selected synthesis of unsymmetric quaterrylene-3,4:13,14-tetracarboximides I (R≠R'). In this case, it is advantageous to use a molar IIb to IIa ratio of from 4:1 to 1:1, in particular of from 2:1 to 1:1.

When nonhalogenated imide IIb is used, it is generally recommended to undertake the reaction under more severe reaction conditions, i.e. to use a nitrogen-containing auxiliary base in addition to a strong alkali metal base.

Suitable solvents are in principle all high-boiling solvents which are stable against bases under the reaction conditions (boiling point >100° C. and above the selected reaction temperature), in which the bases used dissolve fully at reaction temperature and the imides IIa and IIb at least partially, preferably fully, so that there are substantially homogeneous reaction conditions. It is possible to use either aprotic (nonpolar-aprotic and polar-aprotic) or protic solvents. It will be appreciated that solvent mixtures may also be used.

Examples of suitable nonpolar-aprotic solvents are hydrogen carbons boiling at >100° C. from the following groups: aliphatics (in particular $C_8$-$C_{18}$-alkanes), unsubstituted, alkyl-substituted and fused cycloaliphatics (in particular unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (in particular benzene which is substituted by from one to three $C_1$-$C_6$-alkyl groups or a $C_5$-$C_8$-cycloalkyl radical) and fused aromatics which may be alkyl-substituted and/or partially hydrogenated (in particular naphthalene which is substituted by from one to four $C_1$-$C_6$-alkyl groups) and mixtures of these solvents.

Examples of preferred nonpolar-aprotic solvents include:

octane, isooctane, nonane, isononane, decane, isodecane, undecane, dodecane, hexadecane and octadecane; cycloheptane, cyclooctane, methylcyclohexane, di-methylcyclohexane, trimethylcyclohexane, ethylcyclohexane, diethylcyclohexane, pro-pylcyclohexane, isopropylcyclohexane, dipropylcyclohexane, butylcyclohexane, tert-butylcyclohexane, methylcycloheptane and methylcyclooctane;

toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene, 1- and 2-ethylnaphthalene; combinations of the aforementioned solvents as may be obtained from the high-boiling, partly or fully hydrogenated fractions from thermal and catalytic cracking processes in crude oil or naphtha processing, for example mixtures of the Exsol® type, and alkylbenzene mixtures of the Solvesso® type.

Particularly preferred nonpolar-aprotic solvents are xylene (all isomers), mesitylene and in particular decalin.

Examples of suitable polar-aprotic solvents are nitrogen-containing heterocycles and aprotic ethers (in particular cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Examples of preferred polar-aprotic solvents include:

quinoline, isoquinoline, quinaldine, pyrimidine, N-methylpiperidine and pyridine;

dimethyl- and tetramethyltetrahydrofuran and dioxane;

diphenyl ether; the diethyl, dipropyl, diisopropyl, di-n-butyl, di-sec-butyl and di-tert-butyl ethers of ethylene glycol, and ethylene glycol methyl ethyl ether, the dimethyl, diethyl, dipropyl, diisopropyl, di-n-butyl, di-sec-butyl and di-tert-butyl ethers of di- and triethylene glycol, and di- and triethylene glycol methyl ethyl ether.

Particular preference is given to diethylene glycol diethyl ether, diphenyl ether and in particular diethylene glycol dimethyl ether.

Examples of suitable protic solvents are monohydric and polyhydric, aliphatic and aromatic alcohols boiling at >100° C. (in particular monohydric $C_4$-$C_{18}$-alkanols, polyhydric $C_2$-$C_4$-alcohols and oligomers thereof such as $C_2$-$C_3$-alkylene glycols which may comprise up to 6 alkylene oxide units, and phenols), ether alcohols (in particular mono-$C_1$-$C_6$-alkyl and phenyl ethers of monomeric and oligomeric $C_2$-$C_3$-alkylene glycols which may comprise up to 6 alkylene oxide units, in particular ethylene glycol mono-$C_4$-$C_6$-alkyl ethers) and amino alcohols (in particular mono-, di- and tri-$C_2$-$C_4$-alcoholamines).

Examples of preferred protic solvents include:

n-butanol, isobutanol, tert-butanol, n-pentanol, isopentanol, 2-methylbutanol, 2-methyl-2-butanol (tert-amyl alcohol), hexanol, 2-methylpentanol, 3-methyl-3-pentanol, heptanol, 1-ethylpentanol, 3-ethyl-3-pentanol, 2,3-dimethyl-3-pentanoi, octanol, 2-ethylhexanol, 2,4,4-trimethyl-2-pentanol, isooctyl alcohol, nonanol, isononyl alcohol, decanol, 2,2,3,4,4-pentamethyl-3-pentanol, isodecyl alcohol, undecanol, dodecanol, tridecanol, isotridecyl alcohol, tefradecanol, pentadecanol, hexadecanol, heptadecanol and octadecanoi;

ethylene glycol, diethylene glycol, triethylene glycol, tetraethylene glycol, pentaethylene glycol and hexaethylene glycol, propylene glycol, 1,3-propanediol, glycerol and 1,2-, 1,3- and 1,4-butanediol;

the monomethyl, monoethyl, monopropyl, monoisopropyl, mono-n-butyl, mono-sec-butyl, mono-tert-butyl, mono-n-pentyl and mono-n-hexyl ethers of ethylene glycol, and ethylene glycol monophenyl ether, and monomethyl, monoethyl, monopropyl, monoisopropyl, mono-n-butyl, mono-sec-butyl, mono-tert-butyl, mono-n-pentyl and mono-n-hexyl ethers of di- and triethylene glycol, and di- and triethylene glycol monophenyl ether;

monoethanolamine, diethanolamine and triethanolamine.

Particularly preferred protic solvents are ethylene glycol and ethanolamine.

The amount of solvent is generally from 1 to 20 g, preferably from 2 to 10 g and more preferably from 2 to 5 g, per g of imide IIa and IIb.

Suitable bases are strong inorganic and organic alkali metal or alkaline earth metal bases, of which the alkali metal bases are particularly suitable. Preferred inorganic bases are alkali metal and alkaline earth metal hydroxides and amides; preferred organic bases are alkali metal and alkaline earth metal alkoxides (especially the $C_1$-$C_{10}$-alkoxides, in particular tert-$C_4$-$C_{10}$-alkoxides), alkali metal and alkaline earth metal (phenyl)alkylamides (especially the bis($C_1$-$C_4$-alkyl)amides) and triphenylmethyl metaiates. Particular preference is given to the alkali metal alkoxides. Preferred alkali metals are lithium, sodium and potassium, of which very particular preference is given to potassium. Particularly suitable alkaline earth metals are magnesium and calcium.

Specific examples of particularly preferred bases include: lithium hydroxide, sodium hydroxide and potassium hydroxide; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide and potassium tert-butoxide; lithium (1,1-dimethyl) octoxide, sodium (1,1-dimethyl)octoxide, potassium (1,1-dimethyl)octoxide, lithium dimethylamide, lithium diethylamide, lithium diisopropylamide, sodium diisopropylamide, triphenylmethyllithium, triphenylmethylsodium and triphenylmethylpotassium.

Very particularly preferred bases are lithium diisopropylamide, sodium methoxide, sodium tert-butoxide, in particular potassium methoxide and potassium hydroxide and especially potassium tert-butoxide.

When the methoxides and the hydroxides are used, and also generally when non-halogenated imides IIb are used, it is recommended to increase the reactivity by adding a nitrogen-containing auxiliary base having low nucleophilic action, unless a nitrogen-containing heterocycle or an alcohol amine is already present as a solvent. Suitable bases are alkylamines liquid at the reaction temperatures, especially tri-$C_3$-$C_6$-alkylamines such as tripropylamine and tributylamine, alcoholamines, especially mono-, di- and tri-$C_2$-$C_4$-alcoholamines such as mono-, di- and triethanolamine, and especially heterocyclic bases such as pyridine, N-methylpiperidine, N-methylpiperidone, N-methylmorpholine, N-methyl-2-pyrrolidone, pyrimidine, quinoline, isoquinoline, quinaldine and in particular diazabicyclononene (DBN) and diazabicycloundecene (DBU).

Suitable use amounts for the auxiliary base are generally from 0.5 to 25 g, preferably from 1 to 10 g, more preferably from 1 to 3 g, in each case per g of imide IIa and IIb.

The alkali metal or alkaline earth metal base is generally used in amounts of from 2 to 20 mol, in particular from 2 to 10 mol, in each case per mole of imide IIa and IIb.

The alkali metal base may be used in solid or in dissolved form. When the alkali metal base is used in combination with a nonpolar-aprotic reaction solvent in which it is not sufficiently soluble, it may be dissolved in an alcohol which has a higher base strength than the alkali metal base. Suitable are in particular tertiary aliphatic alcohols which may contain aryl substituents and have a total of from four to twelve carbon atoms, for example tert-butanol, 2-methyl-2-butanol (tert-amyl alcohol), 3-methyl-3-pentanol, 3-ethyl-3-pentanol, 2-phenyl-2-pentanol, 2,3-dimethyl-3-pentanol, 2,4,4-trimethyl-2-pentanol and 2,2,3,4,4-pentamethyl-3-pentanol.

The reaction temperature is typically from 70 to 210° C., preferably from 120 to 180° C.

Especially in the absence of an auxiliary base, it may be advantageous for the preparation of unsymmetric quaterrylene-3,4:13,14-tetracarboximides to initially select a reaction temperature in the upper range in order to deprotonate the imide IIa in the 9-position. The subsequent coupling reaction with the halogenated imide IIb may then generally be carried out at lower temperature, which is recommended especially in the presence of base-labile substituents (e.g. cyclohexyl) on the imide nitrogen atom.

The reaction time is generally from 1 to 3 h when halogenated imides IIb are used and from 2 to 12 h when nonhalogenated imides IIb are used.

In terms of process technology, the procedure when non-halogenated imides IIb are used, i.e. in particular a homocondensation, is appropriately as follows:

Solvent, base and, if appropriate, auxiliary base are heated for homogenization under protective gas, and imide IIa and imide IIb, if appropriate after preceding cooling under protective gas, are added and the mixture is heated to the desired reaction temperature with stirring and under protective gas for the desired time. After cooling to room temperature, the quaterrylene-3,4:13,14-tetracarboximides I are precipitated by adding a protic solvent which dissolves the other components, for example $C_1$-$C_6$-alcohols or water. The precipitate is filtered off and washed with one of the solvents mentioned, in particular with one of the alcohols.

When halogenated imides IIb are used, the procedure in process technology terms may be the same as when nonhalogenated imides IIb are used. However, it is also possible initially to heat only a mixture of imide IIa, base, if appropriate auxiliary base, and solvent to a temperature in the range of from 120 to 210° C. with stirring and under protective gas (deprotonation) and to add the imide IIb subsequently, if appropriate after lowering the temperature to from 50 to 120° C.

Occasionally, it may be appropriate to subject the reaction product to an oxidation. In the simplest case, this may be effected by blowing atmospheric oxygen into the still-warm reaction mixture. However, it also possible to add oxidizing agents, preferably hydrogen peroxide, but also aldehyde-containing sugars, e.g. glucose, especially after the reaction.

For further purification, the products I may be recrystallized, for example, from a mixture of halogenated solvents such as chloroform and methylene chloride, and alcohols such as methanol, ethanol and isopropanol. Alternatively, column chromatography on silica gel may also be undertaken using methylene chloride or acetone as the eluent.

A further purification method consists in recrystallizing the products I from N,N-disubstituted aliphatic carboxamides such as N,N-dimethylformamide and N,N-dimethylacetamide, or nitrogen heterocycles such as N-methylpyrrolidone, or mixtures thereof with alcohols such as methanol, ethanol and isopropanol, or washing them with these solvents.

Finally, the products I may also be fractionated from sulfuric acid.

With the aid of the process according to the invention, it is possible to prepare the quaterrylene-3,4:13,14-tetracarboximides I in good yields, (generally of from 30 to 60%) and high purities (typically from 90 to 99%) in an economic manner in one step. Quaterrylene-3,4:13,14-tetracarboximides I substituted either symmetrically or unsymmetrically on the imide nitrogen atoms are obtainable in an advantageous manner.

EXAMPLES

Examples 1 to 7

A mixture of y g of the solvent S, b g of potassium tert-butoxide as a base and if appropriate h g of diazabicyclononene (DBN) or diazabicycloundecene (DBU) as an auxiliary base was heated to 100° C. in a nitrogen atmosphere with stirring for homogenization. After cooling to room temperature, x g of perylene-3,4-dicarboximide II (or $x_a$ g of the imide IIa and $x_b$ g of the imide IIb) were added and the mixture heated to T° C. under nitrogen.

After a continued stirring time of t h at T° C. under nitrogen, cooling to room temperature and, if appropriate, adding 300 ml of methanol for complete precipitation, the precipitate formed was filtered off, washed successfully with cold solvent S, methanol, 10% by weight sulfuric acid and water until the effluent was colorless, and dried at 100° C. under reduced pressure. For further purification, the crude product from Example 2 was subjected to a fractional crystallization from sulfuric acid. The crude product from Example 3 was recrystallized from N-methylpyrrolidone, Further details of these experiments and their results are compiled in the following table.

—N=$CR^1$—, —C≡C—, —$CR^1$=$CR^1$—, —CO—, —SO— and/or —$SO_2$— moieties and which may be mono- or polysubstituted by:

(i) $C_1$-$C_{12}$-alkoxy $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(ii) aryl or hetaryl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1{}_2$, hydroxyl, mercapto, halogen cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be substituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by

TABLE

| Ex. | x [g] | Imide II | y [g] | Solvent S | h [g] | Auxiliary base | Base b [g] | t [h] | T [° C.] | Yield [g]/[%] | Purity [%] |
|---|---|---|---|---|---|---|---|---|---|---|---|
| 1 | 24 | IIa1* | 60 | Diethylene glycol dimethyl ether | 25 | DBN | 20 | 8 | 130 | 12.9/50 | 93 |
| 2 | 24 | IIa1 | 100 | Ethylene glycol monobutyl ether | 25 | DBN | 40 | 4 | 160 | 11.3/44 | 95 |
| 3 | 24 | IIa1 | 60 | Ethanolamine | 50 | DBU | 40 | 6 | 170 | 13.8/45 | 99 |
| 4 | 24 | IIa1 | 80 | Diethanolamine | 25 | DBN | 35 | 8 | 140 | 7.9/32 | 97 |
| 5 | 20 | IIa2** | 300 | Quinoline | — | — | 20 | 8 | 200 | 7.3/34 | 92 |
| 6 | 14 | IIa1 | 60 | Diethylene glycol dimethyl ether | 50 | DBU | 40 | 6 | 190 | 5.3/21 | 90 |
|   | 12 | IIb*** |   |   |   |   |   |   |   |   |   |

*IIa1: N-(2,6-Diisopropylphenyl)perylene-3,4-dicarboximide
**IIa2: N-Phenylperylene-3,4-dicarboximide
***IIb: 9-Bromo-N-(2,6-diisopropylphenyl)perylene-3,4-dicarboximide

What is claimed is:

1. A process for preparing quaterrylene-3,4:13,14-tetracarboximides of the general formula I

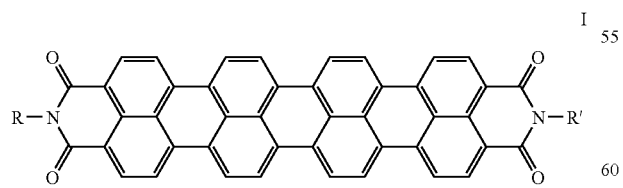

I in which the variables are each defined as follows:
R, R' are each independently:
  hydrogen;
  (A) $C_1$-$C_{30}$-alkyl whose carbon chain may be interrupted by one or more —O—, —S—, —$NR^1$—, one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a -U-aryl radical which may be mono- or polysubstituted by the above radicals specified as substituents for the aryl radicals (ii), where U is an —O—, —S—, —$NR^1$—, —CO—, —SO— or —$SO_2$— moiety;

(B) $C_3$-$C_8$-cycloalkyl, to which may be fused further saturated or unsaturated 5- to 7-membered rings whose carbon skeleton may be interrupted by one or more —O—, —S—, —$NR^1$—, —N=$CR^1$—, $CR^1$=$CR^1$—, —CO—, —SO— and/or —$SO_2$— moieties, where the entire ring system may be substituted once or more than once by: the (i), (ii), (iii), (iv) radicals, and/or (v) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy $C_1$-$C_6$-alkylthio, —C=CR$^1$, —CR$^1$CR$^1_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl and/or the above radicals specified as substituents for alkyl;

(C) aryl or hetaryl, to which may be fused further saturated or unsaturated 5- to 7-membered rings whose carbon skeleton may be interrupted by one or more —O—, —S—, —NR$^1$, —N=CR$^1$—, —C≡C—, —CR$^1$=CR$^1$—, —CO—, —SO— and/or —SO$_2$— moieties, where the entire ring system may be substituted by the (i), (ii), (iii), (iv), (v) radicals, and/or aryl- and/or hetarylazo, each of which may be substituted by $C_1$-$C_{10}$-alkyl $C_1$-$C_6$-alkoxy and/or cyano;

$R^1$ is hydrogen or $C_1$-$C_{18}$-alkyl, where the $R^1$ radicals may be the same or different when they occur more than once;

$R^2$, $R^3$ are each independently hydrogen;

$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;

aryl or hetaryl, to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by $C_1$-$C_{12}$-alkyl and/or the above radicals specified as substituents for alkyl, which comprises reacting a perylene-3,4-dicarboximide of the general formula IIa

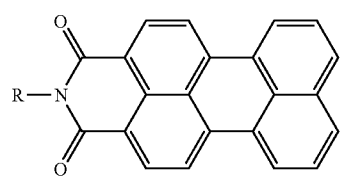

IIa in the presence of a base-stable, high-boiling, organic solvent and of a strong alkali metal base or alkaline earth metal base, at a temperature of from 50 to 210° C., with a perylene-3,4-dicarboximide of the general formula IIb

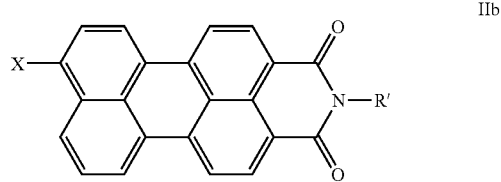

IIb in which X is hydrogen, bromine or chlorine.

2. The process according to claim 1, which is used to prepare quaterrylene-3,4:13,14-tetracarboximides of the formula I, in which the variables are each defined as follows:

R, R' are each independently:

hydrogen;

$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy and/or a 5- to 7-membered heterocyclic radical bonded via a nitrogen atom which may comprise further heteroatoms and be aromatic;

$C_5$-$C_8$-cycloalkyl whose carbon skeleton may be interrupted by one or more —O—, —S— and/or —NR$^1$— moieties, and/or which may be mono- or polysubstituted by $C_1$-$C_6$-alkyl;

aryl or hetaryl which may be mono- or polysubstituted by $C_1$-$C_{18}$-alkyl, $C_1$-$C_6$-alkoxy, cyano, halogen, —CONHR$^2$ and/or aryl- or hetarylazo, each of which may be substituted by $C_1$-$C_{10}$-alkyl, $C_1$-$C_6$-alkoxy or cyano;

$R^1$ is hydrogen or $C_1$-$C_6$-alkyl;

$R^2$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxyl, carboxyl or cyano.

3. The process according to claim 1, wherein an aprotic organic solvent is used.

4. The process according to claim 1, wherein a protic organic solvent is used.

5. The process according to claim 1, wherein the base used is a strong inorganic or organic alkali metal base.

6. The process according to claim 1, wherein the base used is an alkali metal alkoxide.

7. The process according to claim 1, wherein a nitrogen base having low nucleophilic action is additionally used as an auxiliary base.

* * * * *